United States Patent
Davila et al.

(10) Patent No.: US 8,475,838 B2
(45) Date of Patent: Jul. 2, 2013

(54) RAPIDLY-DISSOLVING PHARMACEUTICAL COMPOSITION FOR INHIBITING OVULATION

(75) Inventors: Pablo Davila, East Windsor, NJ (US); Paola Henar Paniagua Marcos, León (ES); Benito Lorenzo Pajuelo, Navarra (ES)

(73) Assignee: Sandoz AG, Basel (CH)

( * ) Notice: Subject to any disclaimer, the term of this patent is extended or adjusted under 35 U.S.C. 154(b) by 1727 days.

(21) Appl. No.: 11/146,314

(22) Filed: Jun. 3, 2005

(65) Prior Publication Data

US 2006/0275362 A1 Dec. 7, 2006

(51) Int. Cl.
*A61K 31/57* (2006.01)
*A61K 31/56* (2006.01)
*A61K 9/20* (2006.01)

(52) U.S. Cl.
USPC .......................................... 424/464; 514/170

(58) Field of Classification Search
None
See application file for complete search history.

(56) References Cited

U.S. PATENT DOCUMENTS

| | | | |
|---|---|---|---|
| 5,569,652 A | 10/1996 | Beier et al. | 514/173 |
| 5,976,570 A | 11/1999 | Greaves et al. | 424/470 |
| 6,667,050 B1 * | 12/2003 | Boissonneault et al. | 424/439 |
| 6,787,531 B1 * | 9/2004 | Hilman et al. | 514/171 |
| 2003/0050289 A1 * | 3/2003 | Schuermann | 514/171 |
| 2005/0220825 A1 * | 10/2005 | Funke et al. | 424/400 |

FOREIGN PATENT DOCUMENTS

| | | | |
|---|---|---|---|
| EP | 0371466 | | 6/1990 |
| WO | 2005030176 | | 4/2005 |
| WO | WO 2005/030176 | * | 7/2005 |
| WO | 2005087194 | | 9/2005 |

* cited by examiner

*Primary Examiner* — Robert A Wax
*Assistant Examiner* — Danah Al-Awadi
(74) *Attorney, Agent, or Firm* — Luedeka Neely Group, P.C.

(57) ABSTRACT

A rapidly-dissolving oral dosage pharmaceutical composition for inhibiting ovulation in a mammal, said composition comprising drospirenone or a pharmaceutically acceptable salt or ester thereof, optionally ethinyl estradiol or a pharmaceutically acceptable salt, ester or ether thereof, a surfactant and at least one pharmaceutically acceptable excipient, wherein the drospirenone has a surface area of less than 10,000 cm$^2$/g.

10 Claims, 1 Drawing Sheet

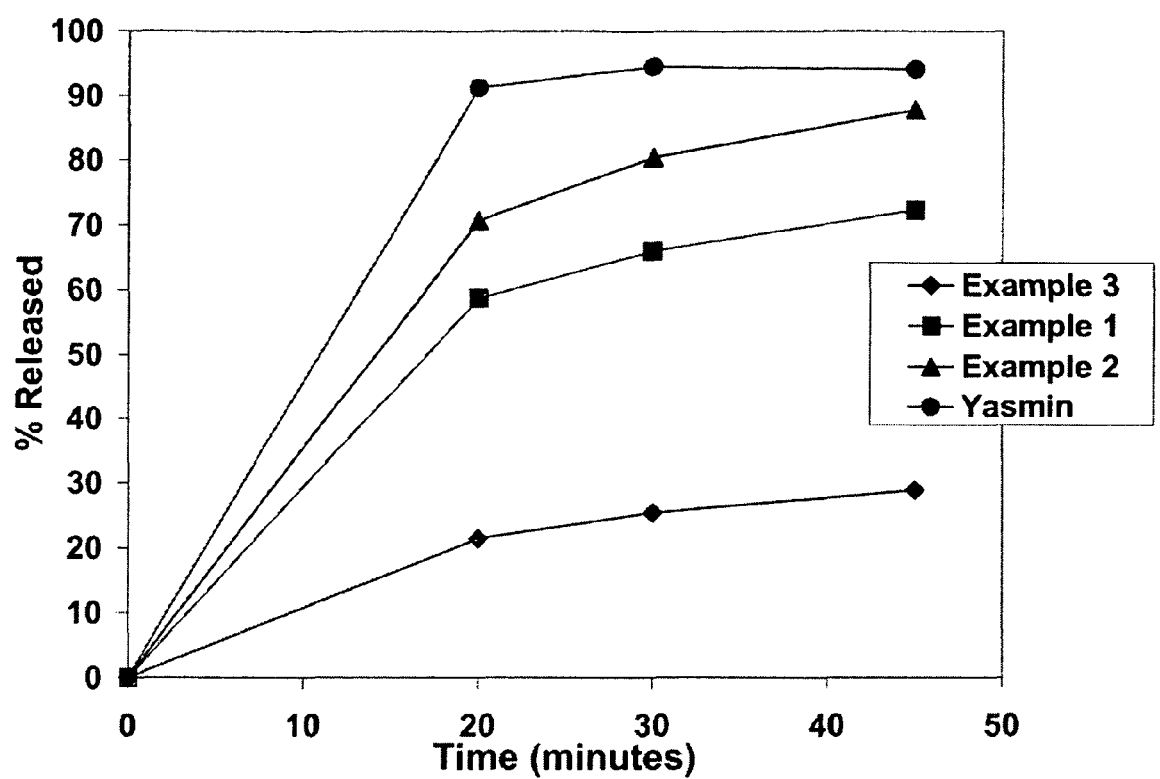

RAPIDLY-DISSOLVING PHARMACEUTICAL COMPOSITION FOR INHIBITING OVULATION

FIELD OF THE INVENTION

The invention relates to a rapidly-dissolving oral dosage pharmaceutical composition for inhibiting ovulation in a mammal, said composition comprising drospirenone, a surfactant, and at least one pharmaceutically acceptable excipient.

BACKGROUND OF THE INVENTION

Drospirenone has the chemical formula (2'S,6R,7R,8R,9S,10R,13S,14S,15S,16S)-1,3',4',6,7,8,9,10,11,12,13,14,15,16,20,21-hexadecahydro-10,13-dimethylspiro[17H-dicyclopropa[6,7:15,16]cyclopenta[a]phenanthrene-17,2'(5'H)-furan]-3,5'(2H)-dione. Drospirenone is a synthetic progestational compound having a molecular weight of 366.49 and a molecular formula of $C_{24}H_{30}O_3$. Ethinyl estradiol has the chemical formula (17α)-19-norpregna-1,3,5(10)-trien-20-yne-3,17-diol. Ethinyl estradiol is a synthetic estrogenic compound having a molecular weight of 296.4 and a molecular formula of $C_{20}H_{24}O_2$.

YASMIN® 28 Tablets is an oral contraceptive regimen consisting of 21 active film-coated tablets, each containing 3.0 mg of drospirenone and 0.030 mg of ethinyl estradiol, and 7 inert film-coated tablets. The inactive ingredients are lactose monohydrate NF, corn starch NF, modified starch NF, povidone 25000 USP, magnesium stearate NF, hydroxypropylmethyl cellulose USP, macrogol 6000 NF, talc USP, titanium dioxide USP, ferric oxide pigment, and yellow NF. The inert film-coated tablets contain lactose monohydrate NF, corn starch NF, povidone 25000 USP, magnesium stearate NF, hydroxypropylmethyl cellulose USP, talc USP, and titanium dioxide USP.

U.S. Pat. No. 5,976,570 describes a process for making a pharmaceutical composition comprising the steps of: (i) preparing an aqueous medium comprising one or more pharmaceutically acceptable surfactants, wherein the quantity of said surfactant or surfactants is sufficient to support a medicinal agent in solution; and (ii) granulating said one or more low dosage medicinal agents in said aqueous medium to form a granulation.

U.S. Pat. No. 6,787,531 describes a pharmaceutical composition comprising from about 2 mg to about 4 mg of micronized drospirenone particles, about 0.01 mg to about 0.05 mg of 17α-ethinyl estradiol, and one or more pharmaceutically acceptable carriers. Micronized is defined as a surface area of greater than 10,000 $cm^2/g$, and the following particle size distribution as determined under a microscope: not more than 2% of the particles in a given batch have a diameter of more than 30 μm, and preferably less than or equal to 20% of the particles have a diameter of greater than or equal to 10 μm and less than or equal to 30 μm, in a pharmaceutical composition.

It would be desirable to prepare a pharmaceutical composition containing drospirenone which does not require micronization of the drospirenone particles in order to achieve rapid dissolution of the drospirenone from the composition.

SUMMARY OF THE INVENTION

The invention provides a rapidly-dissolving oral dosage pharmaceutical composition for inhibiting ovulation in a mammal, said composition comprising drospirenone or a pharmaceutically acceptable salt or ester thereof, optionally ethinyl estradiol or a pharmaceutically acceptable salt, ester or ether thereof, a surfactant and at least one pharmaceutically acceptable excipient, wherein the drospirenone has a surface area of less than 10,000 $cm^2/g$.

According to another aspect, the invention provides a method of inhibiting ovulation in a mammal, in particular, a human female, comprising administering to said mammal, a rapidly-dissolving oral dosage pharmaceutical composition comprising drospirenone or a pharmaceutically acceptable salt or ester thereof, optionally ethinyl estradiol or a pharmaceutically acceptable salt, ester or ether thereof, a surfactant and at least one pharmaceutically acceptable excipient, wherein the drospirenone has a surface area of less than 10,000 $cm^2/g$.

According to another aspect, the invention provides a method for preparing a rapidly-dissolving oral dosage pharmaceutical composition for inhibiting ovulation in a mammal, said composition comprising drospirenone or a pharmaceutically acceptable salt or ester thereof, optionally ethinyl estradiol or a pharmaceutically acceptable salt, ester or ether thereof, a surfactant and at least one pharmaceutically acceptable excipient, wherein the drospirenone has a surface area of less than 10,000 $cm^2/g$, said method comprising:
(a) combining drospirenone or a pharmaceutically acceptable salt or ester thereof, optionally ethinyl estradiol or a pharmaceutically acceptable salt, ester or ether thereof and at least one excipient to form a premix;
(b) adding a solvent and a surfactant to the premix formed in Step (a) to form a wet granulation;
(c) drying the wet granulation to form dried granules, and optionally milling the dried granules; and
(d) optionally mixing at least one excipient with the granules to form a pharmaceutical composition.

The pharmaceutical compositions of the invention do not require micronization of the drospirenone in order to achieve rapid dissolution of the drospirenone from the composition.

BRIEF DESCRIPTION OF THE DRAWINGS

FIG. 1 is a release profile comparison of two drospirenone compositions prepared according to the invention (Examples 1 and 2), a comparative drospirenone composition (Example 3), and a commercially-available drospirenone composition (YASMIN®).

DESCRIPTION OF THE INVENTION

The present invention relates to a rapidly-dissolving oral dosage pharmaceutical composition for inhibiting ovulation in a mammal, said composition comprising drospirenone or a pharmaceutically acceptable salt or ester thereof, optionally ethinyl estradiol or a pharmaceutically acceptable salt, ester or ether thereof, a surfactant and at least one pharmaceutically acceptable excipient, wherein the drospirenone has a surface area of less than 10,000 $cm^2/g$. Surface area may be determined, for example, using gas adsorption (BET) or the Blaine Method. Preferably, the drospirenone is in the form of particles wherein greater than 2% of the drospirenone particles in the pharmaceutical composition have a diameter of at least 30 μm, as determined under a microscope. Particle size may be determined, for example, using microscopy. As used herein, "rapidly dissolving" means the release of drospirenone or a pharmaceutically acceptable salt or ester thereof, of at least 55% within about 20 minutes, preferably greater than 70% within about 45 minutes, from a tablet preparation containing 3 mg of drospirenone in 900 mL of water at 37° C. (±0.5° C.), as determined by the USP XXIII Paddle Method using a USP dissolution test apparatus 2 at a stirring rate of 50 rpm.

Drospirenone has the chemical formula (2'S,6R,7R,8R,9S, 10R,13S,14S,15S,16S)-1,3',4',6,7,8,9,10,11,12,13,14,15,16, 20,21-hexadecahydro-10,13-dimethylspiro[17H-dicyclopropa[6,7:15,16]cyclopenta[α]phenanthrene-17,2'(5'H)-furan]-3,5'(2H)-dione. Drospirenone is a synthetic progestational compound having a molecular weight of 366.49 and a molecular formula of $C_{24}H_{30}O_3$. It is within the scope of the invention that a salt, ester or prodrug of drospirenone may be employed in the pharmaceutical compositions of the invention, i.e., an oxyiminopregnane carbolactone. Drospirenone is commercially available from Industriale Chimica.

Ethinyl estradiol has the chemical formula (17α)-19-norpregna-1,3,5(10)-trien-20-yne-3,17-diol. Ethinyl estradiol is a synthetic estrogenic compound having a molecular weight of 296.4 and a molecular formula of $C_{20}H_{24}O_2$. It is within the scope of the invention that a salt, ester, or ether of ethinyl estradiol may be included in the pharmaceutical compositions of the invention.

The pharmaceutical compositions of the invention preferably comprise drospirenone or a pharmaceutically acceptable salt or ester thereof, in an amount corresponding to a daily dosage of from about 2 mg to about 4 mg, more preferably from about 2.5 mg to about 3.5 mg. Optionally, the compositions of the invention include ethinyl estradiol. The amount of ethinyl estradiol or a pharmaceutically acceptable salt, ester or ether thereof, preferably corresponds to a daily dosage of from about 0.01 mg to about 0.05 mg, more preferably from about 0.015 mg to about 0.04 mg. Most preferably, the pharmaceutical compositions comprise an amount of drospirenone corresponding to a daily dosage of about 3 mg and ethinyl estradiol in an amount corresponding to a daily dosage of about 0.03 mg.

The pharmaceutical compositions of the invention contain at least one surfactant. Suitable surfactants include anionic, nonionic, cationic and amphoteric surfactants. A mixture of surfactants may also be used. Examples of nonionic surfactants include, but are not limited to, the following:

1) Reaction products of a natural or hydrogenated castor oil and ethylene oxide. The natural or hydrogenated castor oil may be reacted with ethylene oxide in a molar ratio of from about 1:35 to about 1:60, with optional removal of the PEG component from the products. The PEG-hydrogenated castor oils, available under the trademark CREMOPHOR, are especially suitable.
2) Polyoxyethylene-sorbitan-fatty acid esters, also called polysorbates, e.g., mono- and tri-lauryl, palmityl, stearyl and oleyl esters of the type known and commercially available under the trademark TWEEN, including the products TWEEN:
   Tween 20 [polyoxyethylene(20)sorbitanmonolaurate]
   Tween 40 [polyoxyethylene(20)sorbitanmonopalmitate]
   Tween 60 [polyoxyethylene(20)sorbitanmonostearate]
   Tween 65 [polyoxyethylene(20)sorbitantristearate]
   Tween 80 [polyoxyethylene(20)sorbitanmonooleate]
   Tween 81 [polyoxyethylene(5)sorbitanmonooleate]
   Tween 85 [polyoxyethylene(20)sorbitantrioleate]

Although PEG itself does not function as a surfactant, a variety of PEG fatty acid esters have useful surfactant properties. Among the PEG fatty acid monoesters, esters of lauric acid, oleic acid and stearic acid are most useful.

3) Polyoxyethylene fatty acid esters, e.g., polyoxyethylene stearic acid esters of the type known and commercially available under the trademark MYRJ.
4) Polyoxyethylene-polyoxypropylene co-polymers and block co-polymers, e.g., of the type known and commercially available under the trademark PLURONIC, EMKALYX and POLOXAMER.
5) Dioctylsulfosuccinate or di-[2-ethylhexyl]-succinate.
6) Phospholipids, in particular, lecithins. Suitable lecithins include, in particular, soybean lecithins.
7) PEG mono- and di-fatty acid esters, such as PEG dicaprylate, also known and commercially available under the trademark MIGLYOL 840, PEG dilaurate, PEG hydroxystearate, PEG isostearate, PEG laurate, PEG ricinoleate, and PEG stearate.
8) Polyoxyethylene alkyl ethers, such as those commercially available under the trademark BRIJ, e.g., Brij 92V and Brij 35.
9) Fatty acid monoglycerides, e.g., glycerol monostearate and glycerol monolaurate.
10) Tocopherol esters, e.g., tocopheryl acetate and tocopheryl acid succinate.
11) Succinate esters, e.g., dioctylsulfosuccinate or related compounds, such as di-[2-ethylhexyl]-succinate.

More preferably, the nonionic surfactant is selected from polyoxyethylene(20)sorbitanmonooleate, glycerol monostearate, glycerol monolaurate, glycerol monopalmitate, glycerol monooleate, glycerol monocaprylate, sodium lauryl sulphate, cetyltrimethyl ammoniumbromide and dioctylsodium sulfosuccinate. Most preferably, the nonionic surfactant is TWEEN 80 (polyoxyethylene(20)sorbitanmonooleate).

Examples of anionic surfactants include, but are not limited to, sulfosuccinates, phosphates, sulfates and sulfonates. Specific examples of anionic surfactants are sodium lauryl sulfate, ammonium lauryl sulfate, ammonium stearate, alpha olefin sulfonate, ammonium laureth sulfate, ammonium laureth ether sulfate, ammonium stearate, sodium laureth sulfate, sodium octyl sulfate, sodium sulfonate, sodium sulfosuccinamate, sodium tridecyl ether sulfate and triethanolamine lauryl sulfate. A preferred anionic surfactant is sodium lauryl sulfate.

The surfactant is preferably present in an amount of from about 0.01 weight percent (wt %) to about 20 wt %, based on the total weight of the pharmaceutical composition. More preferably, the surfactant is present in an amount of from about 1 wt % to about 10 wt %, based on the total weight of the composition.

It is within the scope of the invention for the pharmaceutical compositions, in addition to drospirenone or a pharmaceutically acceptable salt or ester thereof, optionally ethinyl estradiol or a pharmaceutically acceptable salt, ester or ether thereof, and surfactant, to include one or more pharmaceutically acceptable excipients. Examples of such excipients are fillers, carriers, diluents, binders, anti-caking agents, amino acids, fibers, solubilizers, disintegrants, lubricants, emulsifiers, flavorants, solvents, buffers, stabilizers, colorants, dyes, anti-oxidants, anti-adherents, preservatives, electrolytes and glidants. A mixture of excipients may also be used. Such excipients are known to those skilled in the art, and thus, only a limited number will be specifically referenced.

Examples of fillers include lactose anhydrous, microcrystalline cellulose, starch, pregelatinized starch, modified starch, dibasic calcium phosphate dihydrate, calcium sulfate trihydrate, calcium sulfate dihydrate, calcium carbonate, lactose, dextrose, sucrose, mannitol and sorbitol. A combination of fillers may also be used. A preferred filler is lactose monohydrate.

Examples of solvents include water, acetonitrile, ethyl acetate, acetone, benzene, toluene, dioxane, dimethylformamide, chloroform, methylene chloride, ethylene chloride, carbon tetrachloride, chlorobenzene, acetone, methanol, ethanol, isopropanol and butanol. A combination of solvents may also be used. A preferred solvent is water.

Examples of lubricants include magnesium stearate, calcium stearate, zinc stearate, talc, propylene glycol, PEG, stearic acid, vegetable oil, sodium benzoate, sodium lauryl sulfate, magnesium lauryl sulfate, mineral oil and polyoxyethylene monostearate. A combination of lubricants may also be used. A preferred lubricant is magnesium stearate.

Examples of binders include starches, e.g., potato starch, wheat starch, corn starch; gums, such as gum tragacanth, acacia gum and gelatin; microcrystalline cellulose, e.g., products known under the registered trademarks Avicel, Filtrak, Heweten or Pharmacel, hydroxypropyl cellulose, hydroxyethyl cellulose and hydroxypropylmethyl cellulose; and polyvinyl pyrrolidone, e.g., Povidone. Preferred binders are corn starch and polyvinylpyrrolidone.

Examples of glidants include silica, magnesium trisilicate, powdered cellulose, starch, talc and tribasic calcium phosphate.

Examples of disintegrants include:
(i) natural starches, such as maize starch, potato starch and the like; directly compressible starches, e.g., Sta-RX® 1500; modified starches, e.g., carboxymethyl starches and sodium starch glycolate, available as Primojel®, Explotab®, Explosol®; and starch derivatives, such as amylose;
(ii) crosslinked polyvinylpyrrolidones, e.g., crospovidones;
(iii) alginic acid and sodium alginate;
(iv) methacrylic acid-divinylbenzene co-polymer salts, e.g., Amberlite® IRP-88; and
(v) cross-linked sodium carboxymethylcellulose, available as, e.g., Ac-Di-Sol®, Primellose®, Pharmacel® XL, Explocel® and Nymcel®ZSX.

Additional disintegrants also include hydroxypropyl cellulose; hydroxypropylmethyl cellulose; croscarmellose sodium; sodium starch glycolate; polacrillin potassium; polyacrylates, such as Carbopol®; magnesium aluminium silicate; and bentonite.

In one embodiment of the invention, the pharmaceutical compositions of the invention are essentially free of a disintegrant. As used herein, "essentially free" means that the pharmaceutical compositions contain less than 1% by weight of a disintegrant.

There are three general methods of preparation of the pharmaceutical compositions of the invention: (1) dry granulation, (2) direct compression and (3) wet granulation. Dry granulation involves mixing the ingredients to be incorporated into the pharmaceutical compositions, slugging the ingredients, dry screening, lubricating and finally compressing the ingredients. Direct compression involves compressing the ingredients to be incorporated into the pharmaceutical compositions directly without modifying the physical nature of the materials.

In one embodiment of the invention, the pharmaceutical composition of the invention is prepared by a wet granulation process comprising:
(a) combining drospirenone or a pharmaceutically acceptable salt or ester thereof, optionally ethinyl estradiol or a pharmaceutically acceptable salt, ester or ether thereof and at least one excipient to form a premix;
(b) adding a solvent and a surfactant to the premix formed in Step (a) to form a wet granulation;
(c) drying the wet granulation to form dried granules, and optionally milling the dried granules; and
(d) optionally mixing at least one excipient with the granules to form a pharmaceutical composition.

Drying techniques useful for drying the particles include spray-drying, fluid bed drying, flash drying, ring drying, micron drying, tray drying, vacuum drying, radio-frequency drying and microwave drying. A preferred drying technique is vacuum drying.

Types of mills which may be used to reduce the size of the particles include fluid energy mill, ball mill or rod mill, hammer mill, cutting mill and oscillating granulator. More specifically, suitable mills include, Quadro, Fryma, Glatt Quick Sieve, Fluidaire, Fitzpatrick (Fitz mill), BTS mill and Tornado. A preferred mill is an oscillating granulator.

The pharmaceutical compositions of the invention may be formulated in solid form, e.g., a tablet, granules, bar, block, disc, capsule, caplet or powder. The pharmaceutical compositions may also be formulated in liquid form, e.g., as a solution, suspension or emulsion. In a preferred embodiment, the pharmaceutical compositions are in the form of a tablet. The tablets may be coated or uncoated.

A packaging unit comprising the pharmaceutical compositions of the invention may be a conventional blister pack or any other form known for this purpose, e.g., a pack comprising the appropriate number of dosage units (in this case at least 21, or for particular applications, 28 or a multiple of 28) in a sealed blister pack with a cardboard, paperboard, foil or plastic backing and enclosed in a suitable cover. Each blister container may conveniently be numbered or otherwise marked, e.g., starting with the first of the at least 21 dosage units that contain the compositions of the invention, optionally followed by 7 or less empty blisters or by the 7 or less dosage units that contain no active agent or that only contain ethinyl estradiol (although the numbering may also start with the first of the 7 or less dosage units that only contain ethinyl estradiol).

It is also envisaged that the pharmaceutical compositions of the invention may be in the form of a parenteral formulation, such as a subcutaneous implant or transdermal formulation. For making implants, the compositions may suitably be formulated together with one or more polymers that are gradually eroded or degraded when in use, e.g., silicone polymers, ethylene vinylacetate, polyethylene or polypropylene.

Transdermal formulations may be prepared in the form of matrices or membranes or as fluid or viscous formulations in oil or hydrogels. For transdermal patches, an adhesive which is compatible with the skin should be included, such as polyacrylate, a silicone adhesive or polyisobutylene, as well as a foil made of, e.g., polyethylene, polypropylene, ethylene vinylacetate, polyvinylchloride, polyvinylidene chloride or polyester; and a removable protective foil made from, e.g., polyester or paper coated with silicone or a fluoropolymer. For the preparation of transdermal solutions or gels, water or organic solvents or mixtures thereof may be used. Transdermal gels may furthermore contain one or more suitable gelling agents or thickeners, such as silicone, tragacanth, starch or starch derivatives; cellulose or cellulose derivatives or polacrylic acids; or derivatives thereof. Transdermal formulations may also contain one or more substances that enhance absorption though the skin, such as bile salts or derivatives thereof and/or phospholipids.

In addition to inhibiting ovulation, the pharmaceutical compositions of the invention possess anti-androgenic properties and may therefore be used in the prevention or treatment of androgen-induced disorders, in particular, acne. Such use may be independent from or concomitant with the use as a contraceptive disclosed above. Furthermore, since drospirenone is an aldosterone antagonist, it has diuretic properties and is therefore suitable for counteracting the water-retentive properties of ethinyl estradiol.

In one embodiment of the invention, the invention relates to a pharmaceutical preparation consisting of a number of separately packaged and individually removable daily dosage units placed in a packaging unit and intended for oral administration for a period of at least 21 consecutive days.

In one embodiment, the preparation further comprises 7 or less said daily dosage units containing no active agent. Alternatively, it is possible to include, in the dosage regimen, a period of 7 days or less during which no dosage units are ingested. For compliance reasons, however, it may be preferred to include an appropriate number of blanks in the preparation, in which case the total number of daily dosage units in the preparation is at least 28.

In an alternative embodiment of the invention, the invention relates to a contraceptive preparation consisting of a number of separately packaged and individually removable daily dosage units placed in a packaging unit and intended for oral administration for a period of at least 28 consecutive days, wherein at least 21 of said daily dosage units comprise the pharmaceutical compositions of the invention.

The following non-limiting examples illustrate further aspects of the invention.

Example 1

Preparation of Tablets Containing Drospirenone.

| Ingredients | mg/tablet | % Total |
|---|---|---|
| Drospirenone | 3.03 mg | 3.78% |
| Lactose Monohydrate | 44 mg | 54.82% |
| Corn Starch | 9 mg | 11.21% |
| Pregelatinized Starch | 15 mg | 18.69% |
| Povidone K 30 | 8 mg | 9.97% |
| Polysorbate 80 | 0.8 mg | 1% |
| Purified Water | q.s. | |
| Magnesium Stearate | 0.4 mg | 0.5% |
| Total: | 80.23 | 99.97% |

Drospirenone was obtained from Industriale Chimica and had a particle size of 30 μm to 90 μm as determined by sieve analysis.

The tablet composition is prepared by mixing Povidone K30, corn starch, pregelatinized starch, lactose and drospirenone, to form a mixture. A 20% Polysorbate 80 aqueous solution is added to the mixture to form a wet granulation. The wet granulation is dried in an oven at 40° C. to form dried granules. The granules are passed through a 1 mm sieve. Magnesium stearate is mixed with the granules. The resulting granulate was pressed into tablet cores by compression using a rotary tablet press.

Example 2

Preparation of Tablets Containing Drospirenone.

| Ingredients | mg/tablet | % Total |
|---|---|---|
| Drospirenone | 3.03 mg | 3.78% |
| Lactose Monohydrate | 44 mg | 54.82% |
| Corn Starch | 9 mg | 11.21% |
| Pregelatinized Starch | 15 mg | 18.69% |
| Povidone K 30 | 8 mg | 9.97% |
| Polysorbate 80 | 0.8 mg | 1% |
| Purified Water | q.s. | |
| Magnesium Stearate | 0.4 mg | 0.5% |
| Total: | 80.23 | 99.97% |

Drospirenone was obtained from Industriale Chimica and had a particle size of 30 μm to 90 μm as determined by sieve analysis.

The tablet composition is prepared by mixing Povidone K30, pregelatinized starch, and drospirenone, to form a mixture. A 20% Polysorbate 80 aqueous solution is added to the mixture to form a wet granulation. The wet granulation is dried in an oven at 40° C. to form dried granules. The granules are passed through a 1 mm sieve. Corn starch and lactose are mixed with the granules. Magnesium stearate is mixed with the granules. The resulting granulate was pressed into tablet cores by compression using a rotary tablet press.

Example 3 (Comparative)

Preparation of Tablets Containing Drospirenone Without a Surfactant.

| Ingredients | mg/tablet | % Total |
|---|---|---|
| Drospirenone | 3.09 mg | 3.86% |
| Ethinyl Estradiol | 0.031 | 0.04% |
| Lactose Monohydrate | 15.44 mg | 19.3% |
| Corn Starch | 12.78 mg | 15.98% |
| Pregelatinized Starch | 44.2 mg | 55.25% |
| Povidone K 30 | 3.4 mg | 4.25% |
| Croscarmellose Sodium | 0.6 mg | 0.75% |
| Yellow Iron Oxide | 0.09 mg | 0.11% |
| Magnesium Stearate | 0.4 mg | 0.5% |
| Total: | 80.03 | 100% |

Drospirenone was obtained from Industriale Chimica and had a particle size of 30 μm to 90 μm as determined by sieve analysis.

The tablet composition is prepared by mixing drospirenone, lactose, corn starch, pregelatinized starch, and croscarmellose sodium, using a high-speed mixer to form a mixture. Povidone K-30, ethinyl estradiol, and yellow iron oxide are dissolved in ethanol and added to the mixture. Water is added to the mixture to form a wet granulation. The wet granulation is dried under vacuum to form dried granules. The granules are passed through a 1 mm sieve. Magnesium stearate is mixed with the granules. The resulting granulate was pressed into tablet cores by compression using a rotary tablet press.

Example 4

Dissolution Profile Comparison of Drospirenone Compositions prepared in Examples 1-3, as compared to YASMIN®.

With reference to the drawings, FIG. 1 is a dissolution profile comparison of the drospirenone compositions prepared in Examples 1-3, and the commercially-available YASMIN®. The percent release of drospirenone from the tablets prepared in Examples 1-3 and the YASMIN® tablets was determined by the USP XXIII Paddle Method using a USP Dissolution Test Apparatus 2 including 6 covered glass vessels and 6 paddles. Tablets were placed in 900 mL of water at a temperature of 37° C. (±0.5° C.) and stirred at 50 rpm. The percent drospirenone released was measured over a period of 45 minutes individually for each of the compositions and YASMIN®, and the mean average of the percent drospirenone released was plotted.

The results of the dissolution profile in FIG. 1 show that the drospirenone compositions prepared according to the invention in Examples 1 and 2 exhibit very similar release profiles as compared to YASMIN®. The results in FIG. 1 also show that at least 60% of the drospirenone is released within 20 minutes from the compositions according to the invention in Examples 1 and 2, while the composition prepared in Example 3 without a surfactant released only about 20% of the drospirenone within 20 minutes.

Example 5

Effect of Tween 80 as a Solubility Enhancer.

The following procedure was used to determine the effect of Tween 80 on the release of drospirenone;
(i) mix drospirenone, which was sieved through a 90 micron screen, and Tween 80 in a test tube;
(ii) add water to the test tube;
(iii) agitate the test tube for approximately 22 hours; and
(iv) assay the supernatant by ultraviolet (UV) spectrophotometry.

TABLE I

Effect of Tween 80 on the Solubility of Drospirenone

| Solubility Enhancer | Concentration of Drug: Solubility Enhancer (parts by weight) | % Increase in the Solubility of Drospirenone as Determined by HPLC |
|---|---|---|
| Water | None | None |
| Tween 80 (Polysorbate 80) | 1:9 | 42% |

The results in Table I clearly show that Tween 80 significantly increases the solubility of drospirenone in water.

While the invention has been described with particular reference to certain embodiments thereof, it will be understood that changes and modifications may be made by those of ordinary skill within the scope and spirit of the following claims:

What is claimed is:

1. A rapidly-dissolving oral dosage pharmaceutical composition for inhibiting ovulation in a mammal, said composition comprising drospirenone or a pharmaceutically acceptable salt or ester thereof, a polyoxyethylene-sorbitan-fatty acid ester surfactant and at least one pharmaceutically acceptable excipient, wherein the drospirenone is in the form of solid particles having a surface area of less than 10,000 $cm^2/g$ and greater than 2% of said particles have a diameter of at least 30 μm, and wherein the surfactant is present in an amount of from about 0.01 wt % to about 20 wt %, based on the total weight of the composition.

2. The composition according to claim 1, wherein the drospirenone is present in an amount of from about 2 mg to about 4 mg.

3. The composition according to claim 1, wherein the polyoxyethylene-sorbitan-fatty acid ester is selected from the group consisting of polyoxyethylene(20)sorbitanmonolaurate, polyoxyethylene(4)sorbitanmonolaurate, polyoxyethylene(20)sorbitanmonopalmitate, polyoxyethylene(20)sorbitanmonostearate, polyoxyethylene(20)sorbitantristearate, polyoxyethylene(20)sorbitanmonooleate, polyoxyethylene(5)sorbitanmonooleate and polyoxyethylene(20)sorbitantrioleate.

4. The composition according to claim 3, wherein the polyoxyethylene-sorbitan-fatty acid ester is polyoxyethylene(20)sorbitanmonooleate.

5. The composition according to claim 1, further comprising a second surfactant selected from the group consisting of sodium lauryl sulfate, ammonium lauryl sulfate, ammonium stearate, alpha olefin sulfonate, ammonium laureth sulfate, ammonium laureth ether sulfate, ammonium stearate, sodium laureth sulfate, sodium octyl sulfate, sodium sulfonate, sodium sulfosuccinamate, sodium tridecyl ether sulfate and triethanolamine lauryl sulfate.

6. The composition according to claim 5, wherein the second surfactant is sodium lauryl sulfate.

7. The composition according to claim 1, wherein the polyoxyethylene-sorbitan-fatty acid ester surfactant is present in an amount of from about 1 wt % to about 10 wt %, based on the total weight of the composition.

8. The composition according to claim 1, wherein the excipient is selected from the group consisting of diluents, binders, anti-caking agents, amino acids, fibers, solubilizers, disintegrants, fillers, lubricants, emulsifiers, flavorants, solvents, buffers, stabilizers, colorants, dyes, anti-oxidants, anti-adherents, preservatives, electrolytes, glidants, carrier materials and mixtures thereof.

9. The composition according to claim 1, wherein the excipient is polyvinylpyrrolidone.

10. The composition of claim 1 in the form of an uncoated tablet.

* * * * *